United States Patent
Banks

[11] B 3,981,183
[45] Sept. 21, 1976

[54] METHOD AND APPARATUS FOR MEASURING A PHYSICAL PROPERTY OF A FLUID MATERIAL THAT VARIES NONLINEARLY RELATIVE TO THE DENSITY OF THE FLUID

[75] Inventor: William B. Banks, Chappell Hill, Tex.

[73] Assignee: Automation Products, Inc., Houston, Tex.

[22] Filed: Oct. 3, 1974

[21] Appl. No.: 511,909

[44] Published under the second Trial Voluntary Protest Program on February 17, 1976 as document No. B 511,909.

[52] U.S. Cl. .............................. 73/61.1 R; 73/32 A
[51] Int. Cl.² .............................................. G01N 9/36
[58] Field of Search ........... 73/53, 54, 61 R, 61.1 R, 73/32 A, 32 R, 1 R

[56] References Cited
UNITED STATES PATENTS

| | | |
|---|---|---|
| 3,310,974 | 3/1967 | Banks.................................... 73/1 R |
| 3,449,940 | 6/1969 | Banks.................................... 73/32 R |
| 3,678,734 | 7/1972 | Mitchell............................. 73/61.1 R |

Primary Examiner—Richard C. Queisser
Assistant Examiner—Joseph W. Roskos
Attorney, Agent, or Firm—Fulbright & Jaworski

[57] ABSTRACT

A method and apparatus for measuring a physical property of a fluid material, such as concentration, that varies nonlinearly relative to the density of the fluid by measuring the density of the fluid and then injecting a fixed amount of a second miscible fluid having a density different from the density of the first fluid, and measuring the density of the combined fluids whereby the differences in the two measurements is an indication of the nonlinear physical property of the first fluid. Recording the measurements on a recorder, and recording the first measurement at a zeroing point on the recorder in which the scale of the recorder is a difference in the first and second measurements versus the property being measured. The zeroing point may be selected at the point where the density measurements are the same for both the first and second measurements.

13 Claims, 4 Drawing Figures

METHOD AND APPARATUS FOR MEASURING A PHYSICAL PROPERTY OF A FLUID MATERIAL THAT VARIES NONLINEARLY RELATIVE TO THE DENSITY OF THE FLUID

BACKGROUND OF THE INVENTION

Various physical properties of fluids such as the concentration of various fluids, for example most acids, vary as a function of density of the fluid. Since many devices are in use for measuring the density of materials, such as shown in my U.S. Pat. Nos. 3,145,559; 3,177,705; and 3,449,940, the density of a fluid may be readily measured to provide a measurement of the property of the fluid which varies directly with the density. However, the properties of some materials, such as the concentration of sulfuric acid, is a curve which both increases and decreases relative to the density of the sulfuric acid and therefore a measurement of density would not give a valid indication of the concentration of sulfuric acid. Furthermore, various properties of materials that do vary with the density of the material are affected by environmental conditions such as temperature, the presence of other fluids, corrosion, and material buildup which affect density measurements and therefore would prevent accurate density measurement.

The present invention is directed to a method and apparatus for measuring a physical property of a material that varies nonlinearly relative to the density of the fluid in which the density of the fluid is measured for determining the value of the property being measured. In addition, the present method and apparatus overcomes errors caused by environmental conditions such as temperature changes, material buildup on the density measuring apparatus, corrosion, and the presence of other materials present in the fluid.

SUMMARY

The present invention is directed to a method and apparatus for measuring a physical property of a fluid material that varies nonlinearly relative to the density of the fluid by first measuring the density of the fluid, then injecting a predetermined or fixed amount of a second miscible fluid having a density different from the density of the first fluid into the first fluid, and then measuring the density of the combined fluids whereby the differences in the two measurements is an indication of the physical property of the first fluid regardless of changes in environmental conditions, such as temperature changes, material buildup, corrosion, and presence of other materials in the fluid which occur after calibration of the density measuring apparatus.

A further object of the present invention is the provision of a method and apparatus for easily measuring the differences in the two measurements by providing a chart on which the scale is the difference between the first and second measurements versus the property being measured and recording the first measurement at a zeroing point wherein the second measurement directly reads the property being measured. The method and apparatus further comprehends selecting the zeroing point on the chart at the point where the density measurements are the same for both the first and second measurements.

Still a further object of the present invention is the provision of a fluid line through which the fluid to be measured is conducted. A fluid loop including a pump and a density measuring apparatus is also provided. A four-way valve may be provided which interconnects the fluid line and the fluid loop for circulating fluids through the fluid line only in a first position and for circulating fluid through the loop in a second position. Means are provided for injecting a fixed amount of a second fluid having a different density from the first fluid into the loop. Measuring means are connected to the density measuring apparatus for measuring the differences in the density of the first fluid and the density of the combined first and second fluids. In addition, zeroing means are provided for placing the measuring means at a zeroing point for the first measurement so that the second measurement directly measures the desired physical property.

Other and further features, and advantages will be apparent from the following description of the preferred embodiment.

BRIEF DESCRIPTION OF THE DRAWINGS

FIG. 4 is a graph showing one method of selecting the zeroing point for calculating the graph of FIG. 3.

DESCRIPTION OF THE PREFERRED EMBODIMENT

While the present invention is useful for measuring various types of physical properties of a fluid material that varies nonlinearly as a function of its density, for purposes of illustration only, the present invention will be described in connection with measuring the concentration of sulfuric acid.

Figure 2:
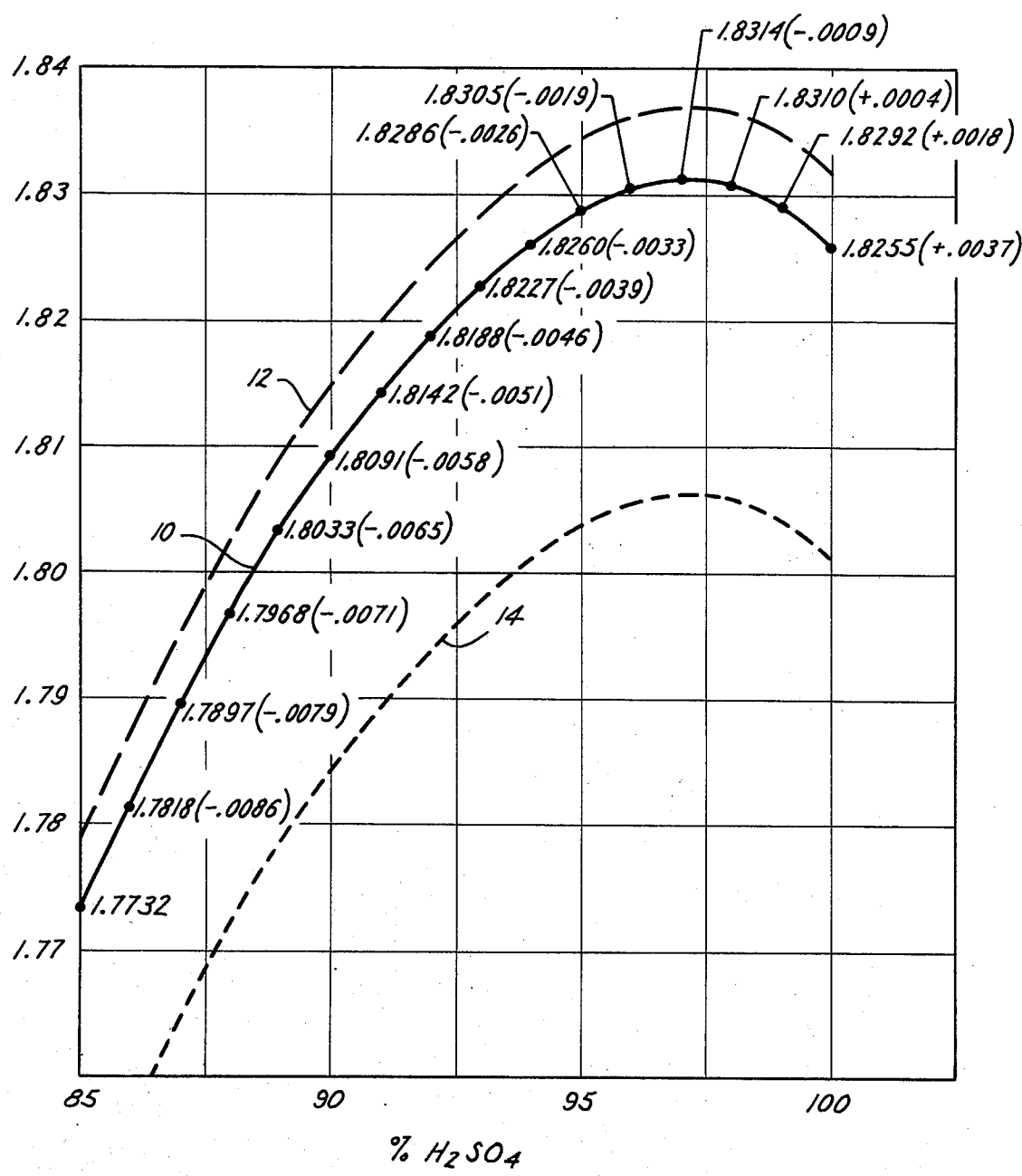
FIG. 2 is a graph showing the characteristic of concentration of sulfuric acid relative to the specific gravity of sulfuric acid.

Referring now to FIG. 2, a graph 10 is shown of the function of the specific gravity, which, of course, is a function of density, relative to the concentration of sulfuric acid at 25° C. It is to be noted that the characteristic of the concentration of sulfuric acid increases in specific gravity nonlinearly, and reaches a peak at approximately 97% concentration after which the specific gravity decreases as the concentration increases. While a measurement of specific gravity would provide the concentration of sulfuric acid at concentration values of less than 94%, it is noted that values of concentration greater than 94% could not be determined by a specific gravity measurement since the specific gravity measurement could be an indication of two different concentration values. That is, a specific gravity measurement of 1.83 could indicate either a concentration of 95.75% or a concentration of 98.75%. Therefore, the usefulness of a single measurement of the density of specific gravity of the sulfuric acid for determining its concentration is limited.

Also, it is noted that the graph 10 gives the specific gravity of sulfuric acid versus its concentration at 25° C. If the temperature of the sulfuric acid changes, then the graph 10 will be shifted vertically upwardly or downwardly. For instance, if the temperature decreases, the resulting graph would be indicated by the dotted graph 12. Obviously, such a change in temperature would adversely affect all measurements of the concentration of the sulfuric acid.

And if the sulfuric acid was in a mixture with a fluid that does not vary nonlinearly in a mixture, and which has a different density from that of the sulfuric acid, the graph 10 would shift and thus be inaccurate. For example, if the sulfuric acid was mixed in a fluid having a density less than the density of sulfuric acid, the graph 10 would shift to graph 14 as indicated in dotted outline. Again, a measurement of density of specific gravity would not give an accurate indication of the concentration of sulfuric acid under those conditions. Other changes in conditions such as material buildup and corrosion on the density measuring apparatus would similarly shift the curve 10 and thus affect the readout of the density measuring apparatus.

The present invention and apparatus is directed to first measuring the density, such as by measuring the specific gravity of the fluid, and then injecting a fixed amount of a second miscible fluid having a density different from the density of the first fluid, and then measuring the density of the combined fluids whereby the differences in the two measurements is an indication of the physical property of the first fluid.

With respect to the sulfuric acid, a first density or specific gravity measurement is taken, and then a fixed amount of a second fluid, such as 1% water, is injected into the sulfuric acid, and a second measurement is taken.

Referring still to FIG. 2, it is noted that the graph 10 includes the specific gravity reading at each percent of concentration of the sulfuric acid. Besides each of the measurements is a parentheses with a plus or a minus quantity which is the value of the change in specific gravity of the sulfuric acid at the specific concentration after 1% of water is injected. For example, at 100% concentration of sulfuric acid the specific gravity measurement is 1.8255. After injection of 1% water, the concentration of specific gravity is then approximately 99% which produces a specific gravity of 1.8292. Therefore, the difference in the specific gravity, at 100% concentration, before and after reading a 1% injection of water is a plus 0.0037 (1.8292–1.8255). Taking another example, the specific gravity reading at 94% concentration is 1.8260 and if a 1% water injection is added, the concentration would be approximately 93% and the specific gravity reading would be 1.8227 indicating a change in specific gravity units of a −0.0033. Therefore, if the change in specific gravity before and after adding water is a plus quantity, then, of course, the concentration is on the right side of the peak of the graph 10. And, if the before and after reading of specific gravity is a minus quantity, then the concentration being measured is on the left side of the peak on the graph 10. And since the curve of the graph 10 is nonlinear, the differences between the before and after readings are different. Therefore, by merely knowing the value of the quantity in the parentheses, which is the direction and amount of the changes between the first and second readings, the amount of the concentration of sulfuric acid is determined.

It is recognized that the addition of 1% water will not reduce the concentration an exact 1%. That is, the addition of 1% water will not reduce a 100% concentration to 99% concentration, but the inaccuracy is insignificant. If desired, this factor may be taken into account in calibrating the graph 10.

It is to be further noted that the present method relies on a difference in two measurements and not on an absolute measurement. The differences would be virtually the same if they were taken along graph 12 or 14 as well as graph 10. Therefore, it is apparent that the present method avoids environmental conditions which uniformly shift the graph, such as changes in temperature, buildup on the density measuring apparatus, the presence of other materials having a different density, as well as other factors.

For example, the present method can determine the physical property, such as the concentration of sulfuric acid, even though the fluid is to be tested is in the presence of another third fluid, such as a hydrocarbon, so long as the third fluid is either immiscible with the second fluid, such as water, which is being added, or the second fluid (water) has a preferential affinity for the first fluid (sulfuric acid) over the third fluid (hydrocarbon).

Figure 3:
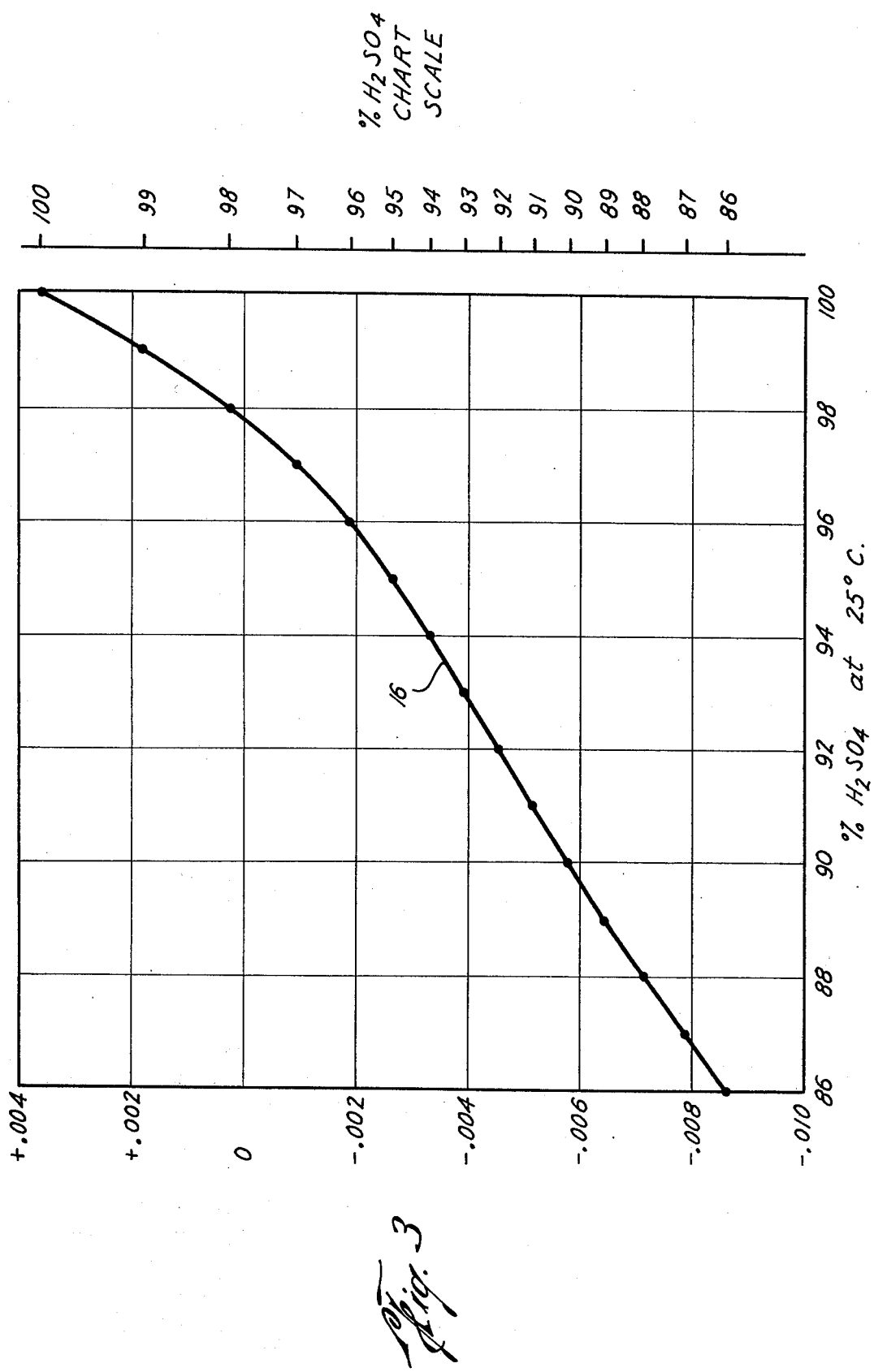
FIG. 3 is a graph showing changes in the specific gravity of sulfuric acid before and after adding 1% of water relative to the concentration of sulfuric acid.

One method of measurement is to first measure the density or specific gravity of the fluid material to be tested. Then, after a fixed amount of a second miscible fluid is injected into a known amount of the first material, a second measurement of the density or specific gravity of the now combined first and second fluids is made. The density or specific gravity of the fluid material is then determined by the difference between the first and second measurements. In order to simplify the measurement, a chart 16 may be prepared, as best seen in FIG. 3, for connection to a chart recorder as will be more fully described hereinafter. The chart 16 is a graph of the differences in specific gravity before and after adding 1% of water to the concentration of sulfuric acid. Graph 16 is plotted from the figures given in FIG. 2. Referring to the previous example, the differences in specific gravity measurements before and after adding water, at 100% concentration, was a plus 0.0037. Therefore, the chart recorder is zeroed after the first reading which would be at 100% to place the specific gravity value 1.8255 at the zeroing point. After adding water, the specific gravity reading will be 1.829 or a gain of plus 0.0037. Thus, referring to FIG. 3, a change of plus 0.0037 indicates a 100% concentration. Similarly, a reading of minus 0.0058 indicates a 90% concentration. Therefore, by using the graph 16 in FIG. 3 on a chart recorder, the chart recorder may be zeroed at the value of the first measurement (90% concentration), and the second measurement taken after adding water which will provide a direct reading of the sulfuric acid concentration.

It is noted in FIG. 3 that zero falls at approximately 97.75% of concentration of sulfuric acid. This means that there is no change between the specific gravity or density reading before and after adding the water. This can best be seen by the enlarged graph in FIG. 4 wherein the reading of specific gravity at 97.75% concentration sulfuric acid is 1.831 and after the addition of 1% water, the reading is 1.831 on the second side of the peak of the graph 10.

Figure 1:
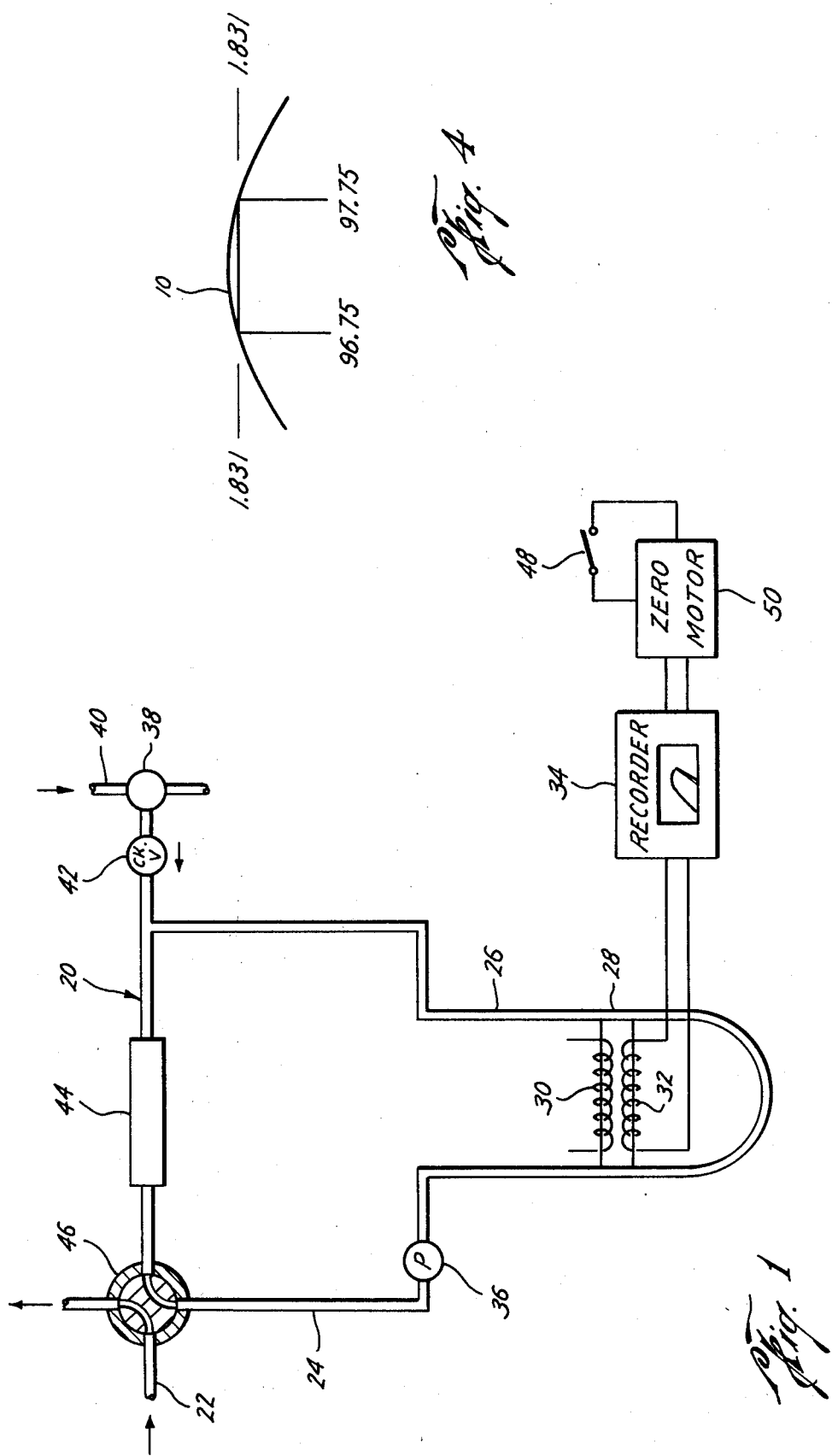
FIG. 1 is a schematic diagram of the apparatus of the present invention.

Referring now to FIG. 1, the apparatus for performing the method of the invention is best seen, and is generally referred to by the reference numeral 20. A flow line 22 is provided through which is flowing the fluid wished to be measured, such as sulfuric acid. A fluid loop 24 is provided which includes a density measuring apparatus 26 which may be any suitable density measuring apparatus such as disclosed in my U.S. Pat. Nos. 3,145,559; 3,177,705; or 3,449,940. Preferably, the vibrating U-tube structure shown in the latter patent is employed which uses a vibrating U-tube body 28 through which fluid is flowed and includes an electrical input signal supplied to an electrical magnetic coil 30 to energize and vibrate the U-tube 28 at the applied frequency. The amplitude of vibration will vary in accordance with the density of the material in or flowing through the U-tube body 28. An electrical magnetic coil 32 is connected to the body 28 and generates a voltage proportional to the amplitude of vibration of the body 28 which will be a measurement of the value or change in the value of the density or specific gravity of the fluid in the body 28. The output from the coil 32 is connected to a conventional chart recorder 34. A fuller description of the structure and operation of the density measuring apparatus 26 is described in my U.S. Pat. No. 3,310,974 and is incorporated herein. In addition, the fluid loop 24 includes a pump 36 for pumping fluid around the loop 24 and through the U-tube body 28.

Means are provided for injecting a second fluid into the closed loop 24 such as a pump 38 for pumping a predetermined amount of fluid from line 40 through a check valve 42 into the loop 24. An expansion joint 44 may be provided in the closed loop 24 to accommodate the volume of the injected fluid and may be of any suitable expansion joint, such as a section of flexible tubing.

A four-way valve 46 is provided interconnecting the fluid line 22 and the fluid loop 24. With the valve 46 in the position shown in FIG. 1, the fluid in line 22 is isolated from the loop 24. However, when the four-way valve 46 is moved to a second position, fluid from the line 22 flows into loop 24, around the loop 24 and out the four-way valve 46 returning to the fluid line 22. In this second position, the fluid to be tested is passed through the loop 24 and the density measuring apparatus 26 and the first reading is taken. The valve 46 is then rotated to its first position as shown in FIG. 1 and a predetermined amount of a second fluid, such as water, is injected by the pump 38 through the check valve 42 into the closed loop 24 where it is mixed with the fluid being tested and circulated by the pump 36 so that the second reading may be taken of the density or specific gravity of the fluid after the injection of the second fluid.

When the first reading of the density of specific gravity of the fluid in line 22 is measured by the density measuring apparatus 26, it is transmitted to the recorder 34. At this time, an electrical switch 48 is actuated to in turn actuate a zero motor 50 which is connected to the recorder 34 to move the chart illustrated in FIG. 3 to bring the zero value on the chart into alignment with the first measurement. After the first reading is taken, the valve 46 is rotated to the second position isolating the fluid in line 22 from the closed loop 24. The second fluid is then injected into the closed loop 24 by means of the pump 38 through check valve 42. The second fluid is mixed in the closed loop 24 by means of the pump 36 and a second measurement is taken by the density measuring apparatus 26 which will be recorded by the recorder 34 on the graph shown in FIG. 3 which provides a direct readout of the concentration of the sulfuric acid.

The method of the present invention is apparent from the foregoing theory and the description of the preferred embodiment. The method, however, comprises measuring the density of the fluid that has a property which varies nonlinearly relative to the density, injecting a fixed amount of a second miscible fluid having a density different from the density of the first fluid, and measuring the density of the combined fluids whereby the differences in the two measurements is an indication of the physical property of the first fluid. The method further comprehends recording the measurement on the chart recorder by recording the first measurement as a zeroing point on a chart recorder in which the scale is a difference in the first and second measurements versus the property being measured. The method further comprehends selecting the zeroing point of the chart at a point where the density measurement is the same for both the first and second measurements.

The present invention, therefore, is well adapted to carry out the objects and attain the ends and advantages mentioned as well as others inherent therein. While a presently preferred embodiment of the invention is given for the purpose of disclosure, numerous changes in the details of construction, arrangement of parts, and steps of the process may be made which will readily suggest themselves to those skilled in the art and which are encompassed within the spirit of the invention and the scope of the appended claims.

What is claimed is:

1. The method of measuring a physical property of a fluid material that varies nonlinearly relative to the density of the fluid comprising,
    measuring the density of the fluid,
    injecting a predetermined amount of a second miscible fluid having a density different from the density of the first fluid into a predetermined amount of the first fluid, and
    measuring the density of the combined fluids whereby the differences in the two measurements is an indication of the physical property of the first fluid.

2. The method of claim 1 including,
    recording the measurements on a chart recorder, zeroing first measurement on a chart in which the scale is a difference in the first and second measurements versus the property being measured.

3. The method of measuring the concentration of an acid in which the concentration is a nonlinear function relative to the specific gravity of the acid comprising,
    measuring the specific gravity of the acid,
    injecting a fixed amount of a miscible second fluid into a certain amount of acid, said second fluid having a specific gravity different from the specific gravity of the acid, and
    measuring the specific gravity of the combined fluids whereby the differences in the two measurements is an indication of the concentration of the acid.

4. The method of claim 3 including,
    recording the first measurement at zero on a chart recording the differences between the first and second measurements as a function of the concentration of the acid whereby the second measurement indicates the concentration of the acid.

5. The method of claim 3 wherein the second fluid is water.

6. The method of claim 4 wherein zero is selected at the point where the density measurement is the same for both the first and second measurements.

7. The method of measuring a physical property of a first fluid that varies nonlinearly relative to the density of the fluid when the first fluid is in solution with a second fluid comprising,
    measuring the density of the fluid, injecting a predetermined amount of a third fluid that is miscible with but has a density different from the density of the first fluid, and which has a preferential affinity for the first fluid over the second fluid, into a predetermined amount of the solution whereby the third fluid combines with the first fluid, but not with the second fluid, and measuring the density of the combined first, second and third fluids whereby the differences in the two measurements is an indication of the physical property of the first fluid.

8. An apparatus for measuring a physical property of a fluid material that varies nonlinearly as a function of the density of the fluid comprising, means for holding said fluid material, a density measuring apparatus connected to said holding means for measuring the density of the fluid in the holding means, means for injecting a fixed amount of a miscible second fluid having a density different from the density of the first fluid into the holding means for obtaining a measurement of the density of combined fluids, and means connected to the density measuring apparatus for measuring the differences in the density of the fluid and the density of the combined first and second fluids.

9. The apparatus of claim 8 wherein the measuring means is a recorder and including, means for zeroing the zeroing point of the recorder to the value of the density measurement of the first fluid.

10. An apparatus for measuring a physical property of a fluid material that varies nonlinearly relative to the density of the fluid comprising, a fluid line through which the fluid is conducted, a fluid loop including a pump and a density measuring apparatus, a valve interconnecting the fluid line and fluid loop for circulating fluid from the line through the loop in one position and for shutting off the line from the loop in another position, means for injecting a fixed amount of a miscible second fluid having a different density from the first fluid into the loop, measuring means connected to the density measuring apparatus for measuring the density of the first fluid and the density of the combined first and second fluids.

11. The apparatus of claim 10 wherein the measuring means is a chart recorder in which the chart records the differences in density between the first fluid and the combined fluids versus the property being measured of the first fluid.

12. The apparatus of claim 11 including zeroing means for placing the first measurement of the chart at zero.

13. An apparatus for measuring a physical property of a fluid material that varies nonlinearly as a function of the density of the fluid comprising, a fluid loop including fluid circulating means and a density measuring apparatus for measuring the density of the fluid in the loop, means for injecting said fluid material into the loop for measuring the density of the fluid material, and means for injecting a predetermined amount of a miscible second fluid having a different density from the first fluid into the loop for measuring the density of the combined first and second fluids.

* * * * *